United States Patent [19]
Kawata et al.

[11] Patent Number: 5,977,377
[45] Date of Patent: Nov. 2, 1999

[54] PROCESS FOR PRODUCING N-ALKYLIMIDAZOLE

[75] Inventors: Naritoshi Kawata; Kazumasa Hirata, both of Osaka, Japan

[73] Assignee: The Nippon Synthetic Chemical Industry Co., Ltd., Osaka, Japan

[21] Appl. No.: 09/206,369

[22] Filed: Dec. 7, 1998

[30]    Foreign Application Priority Data

Dec. 10, 1997    [JP]    Japan ..................................... 9-362247

[51] Int. Cl.$^6$ ....................... C07D 233/58; C07D 233/68
[52] U.S. Cl. ..................... 548/333.5; 548/316.4; 548/321.5; 548/322.5; 548/323.5; 548/324.1; 548/325.5; 548/326.1; 548/327.1; 548/328.1; 548/329.5; 548/330.1; 548/337.1; 548/341.5; 548/342.5; 548/343.1; 548/343.5; 548/345.1; 548/346.1
[58] Field of Search ............... 548/316.4, 321.5, 548/322.5, 323.5, 324.1, 325.5, 326.1, 327.1, 328.1, 329.5, 330.1, 333.5, 337.1, 341.5, 342.5, 343.1, 343.5, 345.1, 346.1

[56]    References Cited

PUBLICATIONS

Derwent 97–389,394, "Used as raw material for, etc" 1997.

R. D. Larsen et al, "Efficient Synthesis of Losartan, A Nonpeptide Angiotensin II Receptor Antagonist", Journal of Organic Chemistry, vol. 59, No. 21, Oct. 21, 1994, pp. 6391–6394.

Database WPI, Section Ch., Week 8150, Derwent Publications Ltd., London, England & JP 56–140972A (Y. Kikukawa), Nov. 4, 1981.

*Primary Examiner*—Patricia L. Morris
*Attorney, Agent, or Firm*—Nikaido, Marmelstein, Murray & Oram LLP

[57]    ABSTRACT

Disclosed is a process for producing an N-alkylimidazole which comprises reacting an imidazole with an N-alkylating agent in an organic solvent in the presence of alkali particles having a specific surface area of 0.6 $M^2/g$ or larger.

7 Claims, No Drawings

PROCESS FOR PRODUCING N-ALKYLIMIDAZOLE

FIELD OF THE INVENTION

The present invention relates to a process for industrially advantageously producing an N-alkylimidazole from an imidazole.

BACKGROUND OF THE INVENTION

N-Alkylimidazoles such as, e.g., 2-alkyl-4-halo-1-(4-halobenzyl)-5-formylimidazoles are useful as raw materials for medicines such as diuretics and hypotensive drugs. In *J. Org. Chem.*, 59, 6391–6394 (1994) is disclosed a method in which 2-n-butyl-4-chloro-5-formylimidazole is reacted with 4-bromobenzyl bromide together with powdery potassium carbonate at −10° C. in N,N-dimethylacetamide to benzylate the imidazole.

However, powdery potassium carbonate has drawbacks in that it is apt to fly off during handling and is highly hygroscopic, although the yield of the target compound in the above method is as high as 93%. Hence, the above method is not always advantageous when practiced on an industrial scale.

SUMMARY OF THE INVENTION

Under these circumstances, an object of the present invention is to provide an industrial process for the production of N-alkylimidazoles, in which an easily handleable chemical is used to smoothly conduct a reaction and to obtain the target compound in a high yield. The present inventors made intensive investigations on alkali particles with respect to their particle diameters and specific surface areas based on the finding that the shape, properties, etc. of alkali particles greatly influence the yield of an N-alkylimidazole. As a result, it has been found that when a reaction is conducted using a commercial particulate alkali, e.g., particulate potassium carbonate, the reaction comes not to proceed any more at the time when the yield has reached about 40 to 50%, and that the specific surface area of the powdery potassium carbonate mentioned above is about 0.5 m²/g at the most. It has been thus found that modifications or variations in the above point influence the yield of a target compound.

The present invention provides a process for producing an N-alkylimidazole which comprises reacting an imidazole with an N-alkylating agent in an organic solvent in the presence of alkali particles having a specific surface area of 0.6 m²/g or larger.

DETAILED DESCRIPTION OF THE INVENTION

The present invention will be explained below in detail.

The imidazole as a starting material may be any compound which contains at least one imidazole ring in the structural formula thereof. However, the imidazole is preferably one represented by the following formula (1):

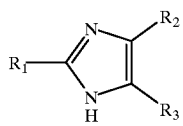

(1)

wherein $R_1$ represents a hydrogen atom, an alkyl, cycloalkyl, phenyl, benzyl, alkenyl, alkynyl, or alkoxy group, or a group formed by replacing a part or all of the hydrogen atoms of any of these substituents with a halogen; and $R_2$ and $R_3$ each represents a hydrogen atom, an alkyl, cycloalkyl, phenyl, benzyl, alkenyl, alkynyl, or alkoxy group, or a group formed by replacing a part or all of the hydrogen atoms of any of these substituents with a halogen, or represents a halogen atom or a nitro, cyano, formyl, or hydroxymethyl group.

Preferred examples of $R_1$ include alkyl groups having 2 to 10 carbon atoms, among which n-butyl is especially important. Preferred examples of $R_2$ include halogens such as chlorine and bromine, among which chlorine is especially preferred. Preferred examples of $R_3$ include nitro, cyano, and formyl, among which formyl is especially preferred.

Examples of the organic solvent include nonhalogenated solvents such as N,N-dimethylacetamide, N,N-dimethylformamide, hexamethylphosphoramide, acetonitrile, ethyl acetate, acetone, and methyl ethyl ketone and halogenated solvents such as ethane dichloride and chloroform. However, nonhalogenated solvents are preferably used. More preferred is N,N-dimethylacetamide.

Examples of the N-alkylating agent include benzyl halides. Specific examples thereof include benzyl halides, o-halobenzyl halides, m-halobenzyl halides, p-halobenzyl halides, o-alkylbenzyl halides, m-alkylbenzyl halides, p-alkylbenzyl halides, o-alkoxycarbonylbenzyl halides, p-alkoxycarbonylbenzyl halides, m-alkoxycarbonylbenzyl halides, o-arylbenzyl halides, m-arylbenzyl halides, p-arylbenzyl halides, o-cyanobenzyl halides, m-cyanobenzyl halides, p-cyanobenzyl halides, o-halomethylbenzoic acids, m-halomethylbenzoic acids, and p-halomethylbenzoic acids. These halides are preferably bromides, chlorides, or iodides.

The most characteristic feature of the present invention resides in that the reaction of an imidazole with an N-alkylating agent in an organic solvent is conducted in the presence of alkali particles having a specific surface area of 0.6 m²/g or larger. Examples of the alkali particles include particles of potassium carbonate, sodium carbonate, sodium hydroxide, potassium hydroxide, sodium nitrate, potassium nitrate, sodium phosphate, and potassium phosphate. However, potassium carbonate particles or sodium carbonate particles are preferably used.

The preferred range of the specific surface area of the alkali particles is from 0.9 to 1.9 m²/g. The specific surface area was measured by the BET method.

The alkali particles are not particularly limited in particle diameter. However, it is preferred to use alkali particles in which the proportion of fine particles is low, because such alkali particles are easy to handle. Specifically, the content of particles each having a size of 74 νm or smaller (particles passing through a standard 200-mesh sieve) is preferably 50% by weight or lower, more preferably 30% by weight or lower. Alkali particles in which the content of 74νm and finer particles exceeds 50% by weight are undesirable in that they are apt to fly off during handling and are highly hygroscopic.

Alkali particles having a surface area within the range specified above can be obtained, for example, by a method comprising melting ordinary alkali particles and drying the melt while foaming the same to obtain porous particles.

Although an imidazole and an N-alkylating agent are used basically in an equimolar proportion, the reaction itself proceeds even when the latter reactant is used in excess. Consequently, the industrially acceptable range of the amount of the latter (N-alkylating agent) is about from 0.8 to 5 mol, especially about from 0.9 to 1.5 mol, per mol of the former (imidazole).

The use amount of alkali particles is generally from 1 to 10 mol, preferably from 1.01 to 2 mol, per mol of the imidazole.

The use amount of an organic solvent is suitably determined as long as the system can be stirred smoothly. In general, however, the use amount of an organic solvent is from 1 to 200 parts by weight, especially from 5 to 50 parts by weight, per part by weight of the sum of the imidazole, alkali particles, and N-alkylating agent. Methods for introducing these ingredients into a reactor are not particularly limited. In general, however, an imidazole and an N-alkylating agent are dissolved in an organic solvent in an inert gas atmosphere or air atmosphere, and alkali particles are then introduced into the solution in a period of from 5 minutes to 5 hours. The reactants are reacted for about further 1 to 8 hours at −20 to 50° C.

For isolating the target compound from the reaction mixture after the reaction, various techniques commonly used by persons skilled in the art can be employed. Examples thereof include a method comprising adding water to the reaction mixture and recovering the resultant crystals, and a method comprising concentrating the reaction mixture, adding water and an appropriate organic solvent to the concentrated reaction mixture to cause phase separation, separating the resultant organic layer therefrom, and washing the same with water.

EXAMPLES

The present invention will be explained below in more detail by reference to Examples.

Example 1

Production of 2-n-butyl-4-chloro-1-(4-bromobenzyl)-5-formylimidazole

This Example is represented by the following reaction scheme.

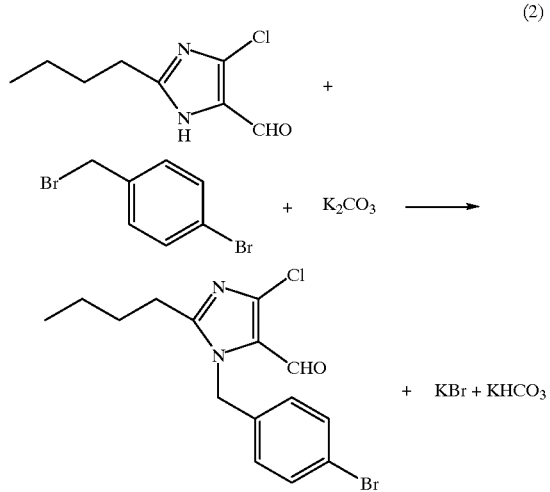

In 200 ml of N,N-dimethylacetamide (DMAC) were dissolved 31.0 g (0.166 mol) of 2-n-butyl-4-chloro-5-formylimidazole and 41.5 g (0.166 mol) of p-bromobenzyl bromide. After this solution was cooled to −10° C., 23.7 g (0.168 mol) of potassium carbonate particles which had a specific surface area of 1.5 m$^2$/g and in which the content of particles each having a diameter of 74 $\mu$m or smaller was 30% by weight were added to the solution over 10 minutes while holding the solution at −10 to −5° C. The resultant mixture was stirred at −10° C. for 2 hours, subsequently heated to room temperature, and then stirred for 2 hours to complete the reaction (which was conducted in an air atmosphere). Thereafter, the reaction mixture was filtered and the filtrate was cooled to 0° C. Thereto was added 320 ml of 15° C. water. The crystals thus precipitated were taken out by filtration to obtain 55.8 g of 2-n-butyl-4-chloro-1-(4-bromobenzyl)-5-formylimidazole having a purity of 99.8% (yield, 98.0%).

Example 2

The same procedure as in Example 1 was conducted, except that in place of the potassium carbonate particles used in Example 1, use was made of the same amount of potassium carbonate particles which had a specific surface area of 1.5 m$^2$/g and in which the content of particles each having a diameter of 74 $\mu$m or smaller was 40% by weight. As a result, 55.8 g of 2-n-butyl-4-chloro-1-(4-bromobenzyl)-5-formylimidazole having a purity of 99.8% was obtained (yield, 98.0%).

Example 3

The same procedure as in Example 1 was conducted, except that in place of the potassium carbonate particles used in Example 1, use was made of the same amount of potassium carbonate particles which had a specific surface area of 1.5 m$^2$/g and in which the content of particles each having a diameter of 74 $\mu$m or smaller was 60% by weight. As a result, 54.1 g of 2-n-butyl-4-chloro-1-(4-bromobenzyl)-5-formylimidazole having a purity of 99.8% was obtained (yield, 95.0%).

Example 4

The same procedure as in Example 1 was conducted, except that in place of the potassium carbonate particles used in Example 1, use was made of the same molar amount of sodium carbonate particles which had a specific surface area of 1.5 m$^2$/g and in which the content of particles each having a diameter of 74 $\mu$m or smaller was 30% by weight. As a result, 55.8 g of 2-n-butyl-4-chloro-1-(4-bromobenzyl)-5-formylimidazole having a purity of 99.8% was obtained (yield, 98.0%).

Example 5

The same procedure as in Example 1 was conducted, except that in place of the potassium carbonate particles used in Example 1, use was made of the same molar amount of potassium nitrate particles which had a specific surface area of 1.5 m$^2$/g and in which the content of particles each having a diameter of 74 $\mu$m or smaller was 30% by weight. As a result, 54.1 g of 2-n-butyl-4-chloro-1-(4-bromobenzyl)-5-formylimidazole having a purity of 99.8% was obtained (yield, 95.0%).

Comparative Example 1

The same procedure as in Example 1 was conducted, except that in place of the potassium carbonate particles used in Example 1, use was made of the same amount of potassium carbonate particles which had a specific surface area of 0.56 m$^2$/g and in which the content of particles each having a diameter of 74 $\mu$m or smaller was 60% by weight. The potassium carbonate particles showed poor handleability because the particles caused dusting during the feeding thereof. As a result, 52.6 g of 2-n-butyl-4-chloro-1-(4- bromobenzyl)-S-formylimidazole having a purity of 99.8% was obtained (yield, 92.5%).

Comparative Example 2

The same procedure as in Example 1 was conducted, except that in place of the potassium carbonate used in Example 1, use was made of the same amount of potassium carbonate particles which had a specific surface area of 0.22 m²/g and in which the content of particles each having a diameter of 74 μm or smaller was 30% by weight. As a result, 26.7 g of 2-n-butyl-4-chloro-1-(4-bromobenzyl)-5-formylimidazole having a purity of 99.8% was obtained (yield, 47.0%).

What is claimed is:

1. A process for producing an N-alkylimidazole which comprises reacting an imidazole with an N-alkylating agent in an organic solvent in the presence of alkali particles having a specific surface area of 0.6 m²/g or larger.

2. The process for producing an N-alkylimidazole according to claim 1, wherein the alkali particles are potassium carbonate particles or sodium carbonate particles.

3. The process for producing an N-alkylimidazole according to claim 1, wherein in the alkali particles, the content of particles each having a diameter of 74 μm or smaller is not higher than 50% by weight.

4. The process for producing an N-alkylimidazole according to claim 2, wherein in the alkali particles, the content of particles each having a diameter of 74 μm or smaller is not higher than 50% by weight.

5. The process for producing an N-alkylimidazole according to claim 1, wherein the N-alkylating agent is a benzyl halide.

6. The process for producing an N-alkylimidazole according to claim 1, wherein the imidazole is represented by the following formula (1):

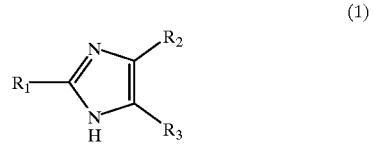

wherein $R_1$ represents a hydrogen atom, an alkyl, cycloalkyl, phenyl, benzyl, alkenyl, alkynyl, or alkoxy group, or a group formed by replacing a part or all of the hydrogen atoms of any of these substituents with a halogen; and $R_2$ and $R_3$ each represents a hydrogen atom, an alkyl, cycloalkyl, phenyl, benzyl, alkenyl, alkynyl, or alkoxy group, or a group formed by replacing a part or all of the hydrogen atoms of any of these substituents with a halogen, or represents a halogen atom or a nitro, cyano, formyl, or hydroxymethyl group.

7. The process for producing an N-alkylimidazole of claim 6, wherein the imidazole represented by formula (1) is a 2-alkyl-4-halo-5-formylimidazole.

* * * * *